United States Patent [19]

Ichikawa et al.

[11] 4,177,182
[45] Dec. 4, 1979

[54] POLYVINYL CHLORIDE SERIES RESIN MEDICAL PRODUCT IMPLEMENTS AND METHOD OF MANUFACTURING THE SAME USING SILOXANE OIL ADDITIVE

[75] Inventors: Toshiji Ichikawa, Tokyo, Japan; Osamu Minoo, Bratislava, Czechoslovakia

[73] Assignee: Terumo Corp., Tokyo, Japan

[21] Appl. No.: 615,978

[22] Filed: Sep. 23, 1975

[30] Foreign Application Priority Data

Oct. 28, 1974 [JP] Japan ............................... 49-123469

[51] Int. Cl.$^2$ ............................................... C08J 3/00
[52] U.S. Cl. ............................................ 260/29.1 SB
[58] Field of Search ............... 260/29.1 SB, 2.5 P, 260/31.8 S, 29.1 SR

[56] References Cited

U.S. PATENT DOCUMENTS

| | | | |
|---|---|---|---|
| 3,034,509 | 5/1962 | Bernstein et al. | 260/29.1 SB |
| 3,428,707 | 2/1969 | Amos et al. | 260/29.1 SB |
| 3,730,931 | 5/1973 | Simoneau et al. | 260/31.8 S |
| 3,790,510 | 2/1974 | Flannigan | 260/31.8 S |
| 3,795,634 | 3/1974 | Nielsen | 260/2.5 P |
| 3,798,189 | 3/1974 | Simoneau et al. | 260/31.8 S |
| 3,940,802 | 3/1976 | Saka et al. | 260/32.4 |
| 3,945,955 | 3/1976 | Ihde, Jr. | 260/29.1 SB |

FOREIGN PATENT DOCUMENTS 691628  5/1953  United Kingdom ............. 260/29.1 SB

OTHER PUBLICATIONS

General Electric—Information re. SS-4250, Feb. '68.

*Primary Examiner*—Joseph L. Schofer
*Assistant Examiner*—Peter F. Kulkosky
*Attorney, Agent, or Firm*—Carroll F. Palmer

[57] ABSTRACT

Polyvinyl chloride series resin compositions comprising 100 parts by weight of polyvinyl chloride series resin, 20 to 80 parts by weight of a plasticizer and 0.2 to 7 parts by weight of silicone oil, which minimize the elution of the plasticizer, and a method of manufacturing polyvinyl chloride series resin compositions which is characterized by emulsifying said silicone oil in advance with part of said plasticizer and adding an emulsion thus formed to said resin compositions.

5 Claims, No Drawings

POLYVINYL CHLORIDE SERIES RESIN MEDICAL PRODUCT IMPLEMENTS AND METHOD OF MANUFACTURING THE SAME USING SILOXANE OIL ADDITIVE

BACKGROUND OF THE INVENTION

This invention relates to polyvinyl chloride series resin compositions which permit small amounts of additives, particularly plasticizers, to be dissolved out and exert harmful effect on the blood.

Hitherto, a large variety of additives have been used with polyvinyl chloride series resin compositions. Particularly, a plasticizer has been added in large quantities to soften the polyvinyl chloride resin. Where such type of polyvinyl chloride resin is applied, for example, to food containers and medical products in particular, those additives have been selected which are as harmless as possible to the human body. However, some of said additives may be proved to exert a harmful effect on the human body by subsequent studies and experiments. Therefore, the additives contained in polyvinyl chloride resin compositions should preferably be prevented from leaching under any condition in which said resin are applied.

A plasticizer, for example, generally consists mainly of phthalic acid ester. Where articles made of polyvinyl chloride series resin compositions containing said phthalic acid ester as a plasticizer are brought into contact with water, said plasticizer is known to be gradually leached out into the water. Though phthalic acid ester leached out into the living body has not been definitely ascertained to have a harmful effect on the health of said living body, yet prevention of the leaching of said plasticizer assumes great importance from the medical point of view.

On the other hand, the nonmigratory plasticizer which has been produced in the past has the drawbacks that it renders polyvinyl chloride series resin compositions less workable due to its high viscosity, has a large molecular weight, is easily saponified because it generally belongs to the polyester series, and is difficult to soften. Therefore, the nonmigratory type of plasticizer is not adapted for use with polyvinyl chloride series resin compositions applied as medical products and food containers.

It is accordingly the object of this invention to provide polyvinyl chloride series resin compositions which prevent additives, particularly, a plasticizer contained therein from being dissolved out, exert little harmful effect on the blood and can be safely applied as food containers, beverage vessels and medical products, and also to provide medical products formed of said polyvinyl chloride series resin compositions and a method of manufacturing said resin compositions.

The present inventors have discovered that incorporation of silicone oil together with the conventional additives in polyvinyl chloride series resin compositions prominently prevents said additives from being dissolved out.

The invention is characterized by impregnating polyvinyl chloride series resin compositions with 0.2 to 7 parts by weight, based on the polyvinyl chloride series resin composition, of at least one kind of silicone oil selected from the group consisting of polymethyl phenyl siloxane, polydimethyl siloxane, polydiphenyl siloxane, polydimethyl methylphenyl siloxane, polydimethyl diphenyl siloxane and polymethyl hydrogen siloxane.

The method of manufacturing polyvinyl chloride series resin compositions according to this invention consists in previously emulsifying silicone oil with part of a plasticizer, adding the remainder of the plasticizer to the resin compositions and thereafter thermally blending both masses. The term polyvinyl chloride series resin, as used herein, means polyvinyl chloride, polyvinylidene chloride, copolymers (including terpolymers) formed mainly of vinyl chloride with a minor amount of other commoner and polymer blends containing polyvinyl chloride as a main component. Comonomers capable of forming copolymers of polyvinyl chloride include vinylidene compounds such as vinyl ester, vinyl ether and vinylidene chloride, lower olefins, vinyl acetate, vinyl bromide, vinyl fluoride, aromatic compounds (for example, styrene), cyclic unsaturated compounds (for example, vinyl pyridine), acrylic acid and derivatives thereof, and conjugate unsaturated compounds such as butadiene.

Other polymers being blended with polyvinyl chloride include styrene-acrylonitrile copolymer and styrene-methylmethacrylate copolymer.

Silicone oil being added to polyvinyl chloride series resin compositions is at least one compound selected from the group consisting of polydimethyl siloxane, polymethyl hydrogen siloxane, polydiphenyl siloxane and polymethyl phenyl siloxane. When directly mixed with polyvinyl chloride series resin compositions, silicone oil having low affinity therefor can not be fully dispersed in said resin compositions. Therefore, it is advised first to emulsify silicone oil with a plasticizer having good affinity therefor and add said emulsion to the polyvinyl chloride series resin compositions. This process enables silicone oil to be fully dispersed in said resin compositions and be coated on the surface thereof.

The proportion of silicone oil is chosen to be 0.2 to 7 parts or preferably 1 to 4 parts by weight based on the added amount of a polyvinyl chloride series resin. Smaller addition of silicone oil than 0.2% by weight fails fully to prevent additives including a plasticizer from being dissolved out. Conversely, larger addition of silicone oil than 7% by weight presents difficulties in molding and processing polyvinyl chloride series resin compositions and fails to provide a homogeneous product of said resin compositions due to the low miscibility of silicone oil therewith.

The proportion of a plasticizer is chosen to be 20 to 80 parts by weight based on 100 parts by weight of polyvinyl chloride series compositions. It is generally preferred to add a larger amount of silicone oil with increase in the proportion of the plasticizer.

For the object of this invention, it is possible to select the kind and proportion of additives including a plasticizer in the same manner as in the past. Silicone oil which itself concurrently acts as a lubricant eliminates the necessity of adding any particular lubricant to polyvinyl chloride series resin compositions.

This invention will be more fully understood by reference to the examples which follow.

A plurality of samples were prepared from pellets of various polyvinyl chloride series resin compositions given in Table 1 below. The pellets were molded into sheets 0.4 mm thick. Values in Table 1 are parts by weight. Throughout Examples 1 to 21, silicone oil was mixed with 20 parts by weight of a plasticizer, and then the mixed mass was added to the polyvinyl chloride series resin compositions.

Table 1

| Composition | \multicolumn{21}{c}{Examples} | | | | | | | | | | | | | | | | | | | | | Controls | | | |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 1 | 2 | 3 | 4 |
| Polyvinyl chloride resin | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| DOP (plasticizer) | 50 | 50 | 0 | 50 | 50 | 0 | 50 | 0 | 50 | 0 | 0 | 50 | 50 | 50 | 50 | 50 | 50 | 0 | 50 | 50 | 0 | 50 | 50 | 0 | 0 |
| Epoxidized soybean oil (plasicizer) | 5 | 0 | 50 | 0 | 0 | 50 | 0 | 50 | 0 | 50 | 50 | 0 | 5 | 5 | 5 | 0 | 0 | 50 | 5 | 5 | 50 | 5 | 5 | 50 | 50 |
| Calcium zinc stearate (stabilizer) | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| Lubricant | 1 | 1 | 1 | 1 | 0 | 0 | 0 | 1 | 1 | 1 | 0 | 0 | 0 | 0 | 0 | 1 | 0 | 0 | 1 | 1 | 0 | 1 | 0 | 1 | 0 |
| Polymethyl phenyl siloxane | 4 | 4 | 4 | | | | | | | | 1 | | | | | | 0.5 | 0.5 | | | 0.5 | | | | |
| Polymethyl hydrodiene siloxane | | | | 2 | | | | | | | | | | | | 1 | | — | | | | | | | |
| Polydimethyl siloxane | | | | | 2 | 2 | | | | | 1 | 2 | | | | | 0.5 | 0.5 | | | 0.5 | | | | |
| Polydiphenyl siloxane | | | | | | | 2 | | | | | | 1 | | | | — | — | | | | | | | |
| Polydimethyl diphenyl siloxane | | | | | | | | 1 | 0.5 | | | | | 1 | | | 0.5 | 0.5 | | | — | | | | |
| Polydimethyl methylphenyl siloxane | | | | | | | | | | 0.5 | | | | | 2 | | 1 | 1 | 0.2 | 7 | — | | | | |

The samples listed in Table 2 below each measuring 20 g were separately immersed in 200 ml of water. The distilled water containing each sample was heated in an autoclave 20 minutes at 121° C., followed by cooling in the air. The distilled water was used as a test liquid. The solution was titrated with 0.01 mol of potassium permanganate. Measurement was made by the specified test method** of the amount of said potassium permanganate consumed by reaction with the material leached from each sample into the water.

Table 2

Results of measuring the amount of material leached out of the sample

| Sample | Consumption of 1/100 mol potassium permanganate* |
|---|---|
| Example 1 | 0.17 |
| 2 | 0.42 |
| 3 | 0.42 |
| 4 | 0.37 |
| 5 | 0.35 |
| 6 | 0.35 |
| 7 | 0.35 |
| 8 | 0.41 |
| 9 | 0.45 |
| 10 | 0.38 |
| 11 | 0.32 |
| 12 | 0.30 |
| 13 | 0.31 |
| 14 | 0.38 |
| 15 | 0.35 |
| 16 | 0.41 |
| 17 | 0.32 |
| 18 | 0.31 |
| 19 | 0.30 |
| 20 | 0.35 |
| 21 | 0.41 |
| Control 1 | 0.80 |
| 2 | 0.72 |
| 3 | 0.85 |
| 4 | 0.84 |

*The amounts of material leached out of the respective samples into the water as converted into the corresponding amounts of potassium permanganate consumed by reaction with said material.
**The specified test method is based on the standards for blood-handling products made of polyvinyl chloride series resin compositions (revised by Notification No. 134 of the Japan Welfare Ministry issued on April 6, 1967).

Test pieces were cut out of Examples 1 and 3 and Control 1 and made into sheets. Test sheets constituting one group were separately immersed in 15% by weight of aqueous solution of lauryl sodium sulfate and allowed to stand 24 hours at 60° C., and those of another group 96 hours at the same temperature. Measurement was made of the lost weight of the test sheet occurring during said immersion, the results being presented in Table 3 below.

Table 3

Results of extraction in aqueous solution of lauryl sodium sulfate

| Sample | Amount of plasticizer leached out based on the total weight of the test sheet (%) | | Amount of plasticizer leached out based on its total weight (%) | |
|---|---|---|---|---|
| | Time of immersion (hrs) | | Time of immersion (hrs) | |
| | 24 | 96 | 24 | 96 |
| Example 1 | 3.7 | 7.5 | 10.9 | 21.6 |
| 2 | 3.7 | 7.2 | 11.6 | 22.7 |
| 3 | 3.5 | 7.0 | 11.0 | 22.1 |
| 4 | 3.9 | 7.2 | 12.1 | 22.3 |
| 5 | 3.7 | 7.4 | 11.6 | 23.2 |
| 6 | 3.2 | 7.5 | 9.90 | 23.2 |
| 7 | 3.2 | 7.5 | 9.80 | 22.9 |
| 8 | 4.0 | 8.0 | 12.4 | 24.8 |
| 9 | 3.9 | 7.8 | 12.0 | 24.0 |
| 10 | 3.8 | 7.7 | 11.7 | 23.7 |
| 11 | 3.5 | 7.2 | 10.8 | 22.2 |
| 12 | 3.7 | 7.7 | 11.4 | 23.7 |
| 13 | 4.0 | 8.0 | 11.5 | 23.0 |
| 14 | 4.1 | 8.0 | 11.9 | 23.2 |
| 15 | 3.8 | 7.8 | 11.0 | 22.5 |
| 16 | 3.2 | 7.5 | 9.9 | 23.2 |
| 17 | 3.2 | 7.5 | 9.9 | 23.2 |
| 18 | 3.6 | 7.8 | 11.1 | 24.0 |
| 19 | 3.7 | 7.8 | 10.7 | 22.5 |
| 20 | 3.0 | 6.7 | 9.0 | 20.1 |
| 21 | 3.1 | 6.9 | 9.6 | 21.3 |
| Control 1 | 4.6 | 20.3 | 12.0 | 53.0 |

Further tests were made on the test sheets of Examples 1 to 21 to determine their toxicity, amounts of additives leached out therefrom and effects of Autoclave sterilization on the test sheets according to the corresponding specified test methods, the results of Examples 1 to 6 being set forth in Table 4 below. The test results of Examples 7 to 21 were almost the same with those shown in Table 4.

Table 4

| | Examples | | | | | |
|---|---|---|---|---|---|---|
| | 1 | 2 | 3 | 4 | 5 | 6 |
| Toxicity cytotoxicity | (—) | (—) | (—) | (—) | (—) | (—) |
| Solubility in blood | (—) | (—) | (—) | (—) | (—) | (—) |
| Amount of additives dissolved out*: | | | | | | |
| Chlorides | Less than 1 ppm | Less than 1 ppm | Less than 1 ppm | Less than 1 ppm | Less than 1 ppm | Less than 1 ppm |
| Ammonium | Less than 1 ppm | Less than 1 ppm | Less than 1 ppm | Less than 1 ppm | Less than 1 ppm | Less than 1 ppm |
| Sulfates | Less than 1 ppm | Less than 1 ppm | Less than 1 ppm | Less than 1 ppm | Less than 1 ppm | Less than 1 ppm |
| Heavy Metals | Less than 1 ppm | Less than 1 ppm | Less than 1 ppm | Less than 1 ppm | Less than 1 ppm | Less than 1 ppm |
| Physical effects of Autoclave sterilization on the test sheets Shrinkage (%): | | | | | | |
| Lengthwise | 1.6 | 1.4 | 1.5 | 1.8 | 1.9 | 1.6 |
| Crosswise | 6.6 | 6.3 | 6.5 | 6.5 | 6.8 | 6.6 |
| Loss of transparency | Slight | Slight | Slight | Slight | Slight | Slight |

Note:
The mark (—) denotes that the test piece is proved to be free from toxicity. The term "crosswise" means the direction in which the test piece was stretched, and the term "lengthwise" shows a direction perpendicular to that in which the test piece was stretched.
*Amounts of additives leached out were determined by the test method specified in Notification No. 134 of the Japan Welfare Ministry described as a note on Table 2.

Further tests were made on the test sheets of Examples 3 and 4 for 100% modulus of elasticity, tensile strength and seal strength under high frequency sealing, the results being given in Table 5 below.

Table 5

| Results of physical tests | | | |
|---|---|---|---|
| Item of test | | Example 3 | Example 4 |
| 100% modulus of elasticity (kg/cm$^2$) | Before sterilization | 75.1 | 88.0 |
| | After sterilization | 71.9 | 78.0 |
| Tensile strength (kg/cm$^2$) | Before sterilization | 182.3 | 191.8 |
| | After sterilization | 153.1 | 181.1 |
| Seal strength (kg) | Before sterilization | 8.7 | 8.6 |
| | After sterilization | 8.8 | 7.9 |
| Water permeability (%) | | 1.2 | 1.4 |

Note:
(1)High frequency sealing was carried out under the following conditions:
Electric power input: Constant
Sealed area: 20 × 8 mm
(2)Water permeability was determined under the following conditions:
Temperature: 20° C.
Humidity: 65%
Allowed to stand: 14 days
(3)The tests on these physical properties were substantially based on the specification of JIS-K-6723 for soft polyvinyl chloride series resin compositions.

Further tests were made on Examples 3 and 4 for the undermentioned items of function, the results being set forth in Table 6 below.

Table 6

| Results of functional tests (based on the test method specified in Notification No. 134 of the Welfare Ministry described in Table 2) | | | |
|---|---|---|---|
| Item of test | | Example 3 | Example 4 |
| Test on a centrifuge Provided with a freezer | Naked eye judgment | — | Good |
| | Pressure test | | Good |
| Permeability to microbes | | No permeability | No permeability |
| Resistance to mold | | Good | Good |

Note:
(1)Kind of bacterium used in the microbe permeability test: Serratia mar. cultured 7 days at 31° C. in the culture plot TGC
(2)Kinds of mold used in the mold resistance test (not set forth in the specification): Cladosporium sp. Candid sp. Curvalaria sp. all cultured 12 days at 30° C. in the culture plot PDA Further tests were made on Example 4 and Control 4 to determine the amount of a plasticizer dissolved out into the calf's serum, the results being indicated in Table 7 below:

Table 7

| Results of measuring the amount of a plasticizer dissolved out into the calf's blood plasma | | | | |
|---|---|---|---|---|
| | Allowed to stand 9 days at 4° C. | | Allowed to stand 23 days at 4° C. | |
| Percentage dissolution of plasticizer | Dissolution based on the total weight of the test sheet (%) | Dissolution based on the total weight of a plasticizer (%) | Dissolutio based on the total weight of the test sheet (%) | Dissolution based on the total weight of a plasticizer (%) |
| Example 4 | 0.00 | 0.00 | 0.00 | 0.00 |
| Control 4 | 0.09 | 0.25 | 0.17 | 0.48 |

In addition to the aforesaid tests, the polyvinyl chloride series resin compositions of this invention were further subjected to various tests such as, a test for survival of red blood cells, triglyceride quantitative test, ultraviolet ray absorption test, test for survival of blood platelets (Rees-Ecker's method), blood coagulation test, and serum preservation test, proving that the subject polyvinyl series resin compositions did not indicate any abnormal condition in the above-listed tests.

As apparent from the results of all the foregoing tests, the polyvinyl chloride series resin compositions according to the various embodiments of this invention more prominently suppress the leaching of additives including a plasticizer than the controls which do not contain silicone oil, exert less harmful effect on the blood and therefore are better adapted for use as medical products such as a blood tubing of an artificial kidney, artificial heart and lungs, catheter and blood bag.

The above-mentioned examples were related to polyvinyl chloride resin included in the polyvinyl chloride series resin compositions. However, this invention enabled any other form polyvinyl chloride series resin compositions to display the same desirable effect, provided it contained silicone oil.

As mentioned above, the present invention provides polyvinyl chloride series resin compositions which noticeably suppress the dissolution of additives including a plasticizer into the living body and also exert little harmful effect on the blood. Accordingly, the subject plyvinyl chloride series resin compositions are not only well adapted for use as food containers, and medical products applied in the collection, preservation and administration of physiological solutions, but also as covering of, for example, electric wires due to excellent weatherability, hydrophobic property and oil resistance.

What we claim is:

1. The method of reducing the leaching of plasticizer from medical product implements made of resin composition consisting essentially of polyvinyl chloride series resin plasticized with 20 to 80% by weight of plasticizer based on the weight of polyvinyl chloride series resin which comprises incorporating in such resin composition 0.2 to 7% by weight of silicone oil based on the weight of polyvinyl chloride series resin, said silicone oil being at least one siloxane compound selected from the group consisting of polymethyl phenyl siloxane, polydimethyl siloxane, polydiphenyl siloxane, polydimethyl phenyl siloxane and polydimethyl hydrogen siloxane.

2. Medical product implements made of resin composition consisting essentially of polyvinyl chloride series resin plasticized with 20 to 80% by weight of plasticizer based on the weight of polyvinyl chloride series resin and 0.2 to 7% by weight of silicone oil based on the weight of polyvinyl chloride series resin, said silicone oil being at least one siloxane compound selected from the group consisting of polymethyl phenyl siloxane, polydimethyl siloxane, polydiphenyl siloxane, polydimethyl phenyl siloxane and polydimethyl hydrogen siloxane, said implement having substantially lower tendency for plasticizer to be leached therefrom by contact with liquids as compared with the same implement absent said silicone oil.

3. Medical product implements of claim 2 wherein said plasticizer comprises a phthalic acid ester.

4. The medical product implements of claim 3 wherein said ester is dioctyl phthalate.

5. The medical product implements of claim 2 wherein said plasticizer comprises epoxidized soybean oil.

* * * * *